(12) United States Patent
Scicinski et al.

(10) Patent No.: US 8,664,247 B2
(45) Date of Patent: Mar. 4, 2014

(54) ACYCLIC ORGANONITRO COMPOUNDS FOR USE IN TREATING CANCER

(75) Inventors: Jan Scicinski, Saratoga, CA (US); Bryan T. Oronsky, Los Altos Hills, CA (US); Robert Wardle, Logan, UT (US); Louis Cannizzo, Ogden, UT (US); Nicholas A. Straessler, North Salt Lake, UT (US)

(73) Assignees: RadioRx, Inc., Mountain View, CA (US); Alliant Techsystems Inc., Arlington, VA (US)

( * ) Notice: Subject to any disclaimer, the term of this patent is extended or adjusted under 35 U.S.C. 154(b) by 0 days.

(21) Appl. No.: 13/593,737

(22) Filed: Aug. 24, 2012

(65) Prior Publication Data

US 2013/0053418 A1 Feb. 28, 2013

Related U.S. Application Data

(60) Provisional application No. 61/527,745, filed on Aug. 26, 2011.

(51) Int. Cl.
| | | |
|---|---|---|
| A61K 31/08 | (2006.01) |
| A61K 31/27 | (2006.01) |
| A61K 31/17 | (2006.01) |
| A61K 31/16 | (2006.01) |
| A61K 31/18 | (2006.01) |
| C07D 401/12 | (2006.01) |
| A61K 31/225 | (2006.01) |
| A61K 31/444 | (2006.01) |
| A61K 31/265 | (2006.01) |
| A61K 31/22 | (2006.01) |
| A61P 35/00 | (2006.01) |
| C07C 205/29 | (2006.01) |

(52) U.S. Cl.
USPC ........... 514/332; 514/716; 514/512; 514/478; 514/484; 514/489; 514/588; 514/626; 514/601; 514/551; 514/547; 514/531; 568/589; 558/276; 546/326

(58) Field of Classification Search
USPC ......... 514/332, 716, 512, 478, 484, 489, 588, 514/626, 601, 551, 547, 531; 568/589; 558/276; 546/326
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |
| 4,765,539 A | 8/1988 | Noakes et al. |
| 5,112,598 A | 5/1992 | Biesalski |
| 5,336,784 A | 8/1994 | Hiskey et al. |
| 5,521,203 A | 5/1996 | Adams et al. |
| 5,556,611 A | 9/1996 | Biesalski |
| 5,579,458 A | 11/1996 | Yokosuka et al. |
| 5,580,988 A | 12/1996 | Dave |
| 5,693,794 A | 12/1997 | Nielsen |
| 5,698,155 A | 12/1997 | Grosswald et al. |
| 5,950,619 A | 9/1999 | van der Linden et al. |
| 5,954,047 A | 9/1999 | Armer et al. |
| 5,970,974 A | 10/1999 | Van Der Linden et al. |
| 6,133,320 A | 10/2000 | Yallampalli et al. |
| 6,245,799 B1 | 6/2001 | Asselin et al. |
| 6,407,236 B1 | 6/2002 | Baraldi et al. |
| 7,163,958 B2 | 1/2007 | Earl et al. |
| 7,507,842 B2 | 3/2009 | Oehler et al. |
| 7,745,643 B2 | 6/2010 | Cannizzo et al. |
| 8,178,698 B2 | 5/2012 | Cannizzo et al. |
| 2002/0137770 A1 | 9/2002 | Nara et al. |
| 2004/0024057 A1 | 2/2004 | Earl et al. |
| 2004/0167212 A1 | 8/2004 | Bednarski et al. |
| 2006/0111272 A1 | 5/2006 | Roberts et al. |
| 2008/0255149 A1 | 10/2008 | Dobler et al. |
| 2008/0256149 A1 | 10/2008 | Bansal et al. |
| 2009/0093644 A1 | 4/2009 | Cannizzo et al. |
| 2009/0163466 A1 | 6/2009 | Bednarski et al. |
| 2011/0130572 A1 | 6/2011 | Cannizzo et al. |
| 2011/0195947 A1 | 8/2011 | Straessler et al. |
| 2012/0149678 A1 | 6/2012 | Oronsky et al. |

FOREIGN PATENT DOCUMENTS

| | | |
|---|---|---|
| DE | 10111049 A1 | 9/2002 |
| EP | 0412211 A1 | 2/1991 |
| WO | WO-9532715 A1 | 12/1995 |
| WO | WO-9636602 A1 | 11/1996 |
| WO | WO-9816485 A1 | 4/1998 |
| WO | WO-9916436 A1 | 4/1999 |
| WO | WO-9959575 A1 | 11/1999 |
| WO | WO-0006143 A1 | 2/2000 |
| WO | WO-0177100 A2 | 10/2001 |
| WO | WO-2004032864 A2 | 4/2004 |
| WO | WO-2004098538 A2 | 11/2004 |
| WO | WO-2004113281 A1 | 12/2004 |
| WO | WO-2005046661 A2 | 5/2005 |
| WO | WO-2007022121 A2 | 2/2007 |
| WO | WO-2007022225 A2 | 2/2007 |

OTHER PUBLICATIONS

Akhavan, Jacqueline, Explosives and Propellants, Kirk-Othmer Encyclopedia of Chemical Technology, Sep. 17, 2004, pp. 719-744.

(Continued)

*Primary Examiner* — San-Ming Hui
*Assistant Examiner* — Kathrien Cruz
(74) *Attorney, Agent, or Firm* — Goodwin Procter LLP

(57) ABSTRACT

The present invention provides acyclic, geminal-dinitro organic compounds, methods of synthesizing the compounds, pharmaceutical compositions, therapeutic methods, and medical kits for treating various conditions using such compounds and pharmaceutical compositions. The compounds and compositions are useful in the treatment of cancer.

13 Claims, 1 Drawing Sheet

(56) References Cited

OTHER PUBLICATIONS

Alderman, D., "A Review of Cellulose Ethers in Hydrophilic Matrices for Oral Controlled-Release Dosage Forms," *Int. J. Pharm. Tech. & Prod. Mfr.*, 1984, vol. 5, No. 3, pp. 1-9.

Ansari, Nabi G., et al., Primary squamous cell carcinoma of the prostate: a rare clinicopathological entity. Report of 2 cases and review of literature, Urol. Int., 2001, pp. 216-219, vol. 66, No. 4 (abstract).

Archibald et al., "Synthesis and X-ray Crystal Structure of 1,3,3-Trinitroazetidine," *J. Org. Chem.*, 1990, vol. 55, pp. 2920-2924.

Australian Examination Report No. 2 on patent application No. 2006279589, dated May 18, 2012.

Bamba et al., "Release Mechanisms in Gelforming Sustained Release Preparations," *Int. J. Pharm.*, 1979, vol. 2, pp. 307-315.

Chawla et al., "Challenges in Polymorphism of Pharmaceuticals", CRIPS vol. 5, No. 1, Jan.-Mar. 2004, pp. 9-12.

Crowder et al., (1999) "Vibrational analysis of high-energy compounds: 1,3,3-trinitroazetidine and 1-acetyl-3, 3-dinitroazetidine," *Journal of Energetic Materials*, vol. 17(1), pp. 49-68.

Crowder et al., Caplus and 1999:171384.

Dave, P., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," *J. Org. Chem.*, 1996, vol. 61, pp. 5453-5455.

Dave, P.R. et al., "Convenient Acylative Dealkylation of Tertiary Amines," *Journal of Organic Chemistry*, 2000, vol. 65, pp. 1207-1209.

During et al., "Controlled Release of Dopamine from a Polymeric Brain Implant: In Vivo Characterization," *Annals of Neurology*, 1989, vol. 25, No. 4, pp. 351-356.

Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.

Feuer et al., "The Mannich reaction of certain dinitro alcohols with glycine and ethanolamine," *Journal of American Chemical Society*, 1954, vol. 76, pp. 5124-5126.

Goodson, J. Max, "Dental Applications," Chapter 6 of Medical Applications of Controlled Release, vol. II, pp. 115-138, CRC Press, Inc., Boca Raton, FL, copyright 1984.

Granelli, P. "SEL 1L and Sqaumous Cell Carcinoma of the Esophagus," *Clinical Cancer Research*, 2004, vol. 10, pp. 5857-5861.

Hiskey et al., "Preparation of 1-Substituted-3,3-Dinitroazetidines," *Journal of Energetic Materials*, 1999, vol. 17, pp. 233-254.

Hiskey et al., caplus an 1993:233785.

Hiskey et al., caplus an 1994:700750.

Hockel et al., "Tumor Hypoxia: Definitions and Current Clinical, Biologic, and Molecular Aspects, " *Journal of the National Cancer Institute*, 2001, vol. 93, No. 4, pp. 266-276.

Howard et al., "Intracerebral Drug Delivery in Rats with Lesion-Induced Memory Deficits," *J. Neursurg.*, 1989, vol. 71, pp. 105-112.

Huguenin et al., "Evaluation of the antitumoral potential of different nitric oxide-donating non-steroidal anti-inflamatory drugs (NO-NSAIDs) on human urological tumor cell lines", Cancer Letters 218 (2005), 163-170 (Abstract, pp. 165,169).

International Search Report and Written Opinion for PCT/US2011/064178 mailed Apr. 17, 2012 (8 pages).

International Search Report and Written Opinion for PCT/US2012/038592 mailed Aug. 10, 2012 (11 pages).

International Search Report for PCT/US2006/031917 mailed Jul. 20, 2007.

International Search Report for PCT/US2006/031722 mailed May 29, 2007.

International Search Report for PCT/US2011/021500 mailed May 3, 2011.

Jia, Q., et al., "NO donors with anticancer activity," Expert Opinion on Therapeutic Patents, vol. 12, No. 6 (2002), pp. 819-826, Great Britain.

Johnson, J. et al., Relationships Between Drug Activity in NCI Preclinical in Vitro and in Vivo Models and Early Clinical Trials, British Journal of Cancer, 2001, pp. 1424-1431, vol. 84, No. 10.

Kashfi, Khosrow, et al., Nitric Oxide-Donating Nonsteroidal Anti-Inflammatory Drugs Inhibit the Growth of Various Cultured Human Cancer Cells: Evidence of a Tissue Type-Independent Effect, The Journal of Pharmacology and Experimental Therapeutics,2002, pp. 1273-1282, vol. 303, No. 3.

Konovalova, N.P., et al., "Nitric oxide donor increases the efficiency of cytostatic therapy and retards the development of drug resistance," Nitric Oxide, vol. 8, No. 1 (Feb. 2003), pp. 59-64.

Kornblum et al., "Oxidative Substitution of Nitroparaffin Salts," *J. Org. Chem.*, 1983, vol. 48, pp. 332-337.

Langer et aL, "Chemical and Physical Structure of Polymers as Carriers for Controlled Release of Bioactive Agents: A Review, " *JMS-Rev. Macromol. Chem. Phys.*, 1983, Ch. 23, pp. 61-126.

Langer, Robert S., et al., eds., "Medical Applications of Controlled Release," vol. 1, Classes of Systems, Ch. 2, pp. 42-67, CRC Press, Inc., Boca Raton, FL, copyright 1984.

Langer, Robert, "New Methods of Drug Delivery," Science, New Series, vol. 249, No. 4976, Sep. 28, 1990, pp. 1527-1533.

Levy, Robert J., "Inhibition of Calcification of Bioprosthetic Heart Valves by Local Controlled-Release Diphosphonate," Science, New Series, vol. 228, No. 4696, Apr. 12, 1985, pp. 190-192.

Ling, C., et al., "Phase I study of CM-Na combined with concurrent radiochemotherapy for advanced esophageal carcinoma (abstract)," Chinese Journal of Cancer, vol. 24, No. 5 (May 2005), (U.S. National Library of Medicine, Bethesda, MD, May 2005).

Lopez-Ferrer, Anna, et al., Differences in the O-Glycosylation Patterns Between Lung Squamous Cell Carcinoma and Adenocarcinoma, Am. J. Clin. Pathol., 2002, pp. 749-755, vol. 118, American Society for Clinical Pathology.

Marchand, A. P. et al., "Additions of X-Y Across the C(3)-N σ-Bond in 1-Aza-3-ethylbicyclo[1.1.0]butane, Novel Routes to 3-Substituted Azetidines," *Journal of Organic Chemistry*, 1994, vol. 59, No. 18, pp. 5499-5501.

Maxwell, P.H., et al., Hypoxia-inducible factor-1 modulates gene expression in solid tumors and influences both angiogenesis and tumor growth, Proc. Natl. Acad. Sci. USA, Jul. 1997, pp. 8104-8109, vol. 94, Medical Sciences.

McKenney, et al., "Synthesis and thermal properties of 1, 3-dinitro-3-(1', 3'-dinitroazetidein-3'-yl) azetidine (tndaz) and its admixtures with 1, 3, 3-trinitroazetidine (TNAZ)," Journal of Energetic Materials, 1998, vol. 16, pp. 199-235.

Mendenhall, William M., et al., Radiation Therapy for Squamous Cell Carcinoma of the Tonsillar Region: A Preferred Alternative to Surgery?, Journal of Clinical Oncology, Jun. 2000, pp. 2219-2225, vol. 18, No. 11.

Morales-Suarez-Varela, Maria M., et al., Impact of Nitrates in Drinking Water on Cancer Mortality in Valencia, Spain, European Journal of Epidemiology, 1995, pp. 15-21, vol. 11.

Muehlstaedt et al., CAPLUS, 1976:89768, 1 page.

Naimi, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., vol. 46, 2003, pp. 995-1004.

Newman et al., "Solid-state analysis of the active pharmaceutical ingredient in drug products", DDT vol. 8, No. 19, Oct. 2003, p. 898-905.

Nitrates and Nitrites Answers to Frequently Asked Questions, Ohio Bureau of Environmental Health, Health Assessment Section, Nov. 1, 2006, 2 pages.

Oxley J. et al., "Thermal Decomposition Pathways of 1,3,3-Trinitroazetidine (TNAZ), Related 3,3-Dinitroazetidium Salts, and $^{15}N$, $^{13}C$, and $^2H$ Isotopomers," *Journal of Physical Chemistry* A, 1997, vol. 101, No. 24, pp. 4375-4383.

Padwa et al., Diastereofacial selectivity in azomethine ylide cycloaddition reactions derived from chiral α-cyanoaminsilanes, Tetrahedron, 1985, vol. 41, No. 17, pp. 3529-3535.

Peiris, S. M. et al., "Structures of dinitroazetidine and three of its carbonyl derivatives," *Journal of Chemical Crystallography*, 2001, vol. 30, No. 10, pp. 647-653.

(56) References Cited

OTHER PUBLICATIONS

Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.
Raleigh et al. "Pharmacokinetics of Isotretinoin (ISO) in Rats Following Oral Dosing or Aerosol Inhalation," *British J. Cancer*, 1999, vol. 80, Suppl. 2, 96, p. 269.
Remington, "The Science and Practice of Pharmacy," 19th Edition, 1995, vol. II, pp. 1495-1562, 1577-1614, and 1660-1692.
Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research, vol. 5, No. 4, pp. 739-745, Apr. 1999.
Sandler, G., "Clinical evaluation of propatylnitrate in angina pectoris," British Medical Journal, vol. 2, No. 5269 (Dec. 30, 1961), pp. 1741-1744.
Sauder, C. "A Preliminary Trial of the Programmable Implantable Medication System for Insulin Delivery," *The New England Journal of Medicine* 1989, vol. 321, No. 9, pp. 574-579.
Sausville, Edward A., et al., Contributions of Human Tumor Xenografts to Anticancer Drug Development, Cancer Research, 2006, pp. 3351-3354, vol. 66, No. 7.
Sefton, M., "Implantable Pumps," *CRC Crit. Rev. Biomed. Eng.*, 1987, vol. 14, No. 3, pp. 201-237.
Shokeir, A., "Squamous Cell Carcinoma of the Bladder: pathology, diagnosis and treatment," *BJU International*, 2004, vol. 93, pp. 216-220.
Sikder et al., "1,3,3-Trinitroazetidine (TNAZ), a melt-cast explosive: synthesis, characterization and thermal behavior," *Journal of Hazardous Materials*, vol. 113, 2004, pp. 35-43.
Simpson, R.L., et al., Characterization of TNAZ, UCRL-ID-119672, Dec. 14, 1994, Lawrence Livermore National Laboratory, 15 pages.
Smolen et al., "Controlled Drug Bioavailability," *Drug Product Design and Performance*, 1984, vol. 1, Ch. 7, pp. 203-237.
Stamler, J.S., et al., "Inhaled ethyl nitrite gas for persistent pulmonary hypertension in infants," The Lancet, Lancet Limited, vol. 360, No. 9350 (Dec. 21, 2002), p. 2077, Great Britain.
Strafford et al.,"Bioreductive drugs into the next millennium," *Anti-Cancer Drug Design*, 1998, vol. 13, pp. 519-528.

Treat, Joseph, et al., "Liposome Encapsulated Doxorubicin Preliminary Results of Phase I and Phase II Trials," Liposomes in the Therapy of Infectious Diseases and Cancer, Proceedings of the Ciba-Geigy-Squibb-UCLA Colloquium at Lake Tahoe, CA, Feb.16-20, 1988, pp. 353-365.
Verma et al., "Osmotically Controlled Oral Drug Delivery," *Drug Dev. Ind. Pharm.*, 2000, vol. 26, No. 7, pp. 695-708.
Watt, Duncan S., et al., Evaluation of 1,3,3-Trinitrozaetidine (TNAZ)—A High Performance Melt-Catable Explosive, Weapons Systems Division Aeronautical and Maritime Research Laboratory, Report No. DSTO-TR-1000, issue date Jul. 2000, 34 pages.
Watt, Duncan S., et al., TNAZ Based Melt-Cast Explosives: Technology Review and AMRL Research Directions, Weapons Systems Division Aeronautical and Maritime Research Laboratory, Report DSTO-TR-0702, issue date Jul. 1998, 1-37 pages.
West, Anthony R., Solid State Chemistry and its Applications, 1988, pp. 358, and 365, Wiley, New York.
Wilson, et aL, "Radiation-activated prodrugs as hypoxia-selective cytotoxins: model studies with nitroarylmethyl quaternary salts," *Anti-Cancer Drug Design*, 1998, vol. 13, pp. 663-685.
Written Opinion of the International Searching Authority for PCT/US2011/021500, mailed May 3, 2011.
Written Opinion of the International Searching Authority for PCT/US06/31722 mailed May 29, 2007.
Written Opinion of the International Searching Authority for PCT/US06/31917 mailed Jul. 20, 2007.
Yarmukhamedov et al., "One-step synthesis of substituted 3,5-dinitropiperidines and 1,5-dinitro-3,7-diazabicyclo(3.3.1)nonanes from 1,3-dinitropropanes," *Russian Chemical Bulletin, International Edition*, 2005, vol. 54, No. 2, pp. 414-420.
Yen, et al., F-FDG Uptake in Squamous Cell Carcinoma of the Cervix Is Correlated with Glucose Transporter 1 Expression, The Journal of Nuclear Medicine, Jan. 2004, pp. 22-29, vol. 45, No. 1.
Zhang et al, caplus an 1998:460439.
Garver et al., "Catalyzed Oxidative Nitration of Nitronate Salts," J. Org. Chem. 1985, vol. 50, No. 10, pp. 1699-1702.
Katritzky et al., "Novel Syntheses of 1,3,3-Trinitroazetidine," J. Heterocyclic Chem., Mar-Apr. 1994, vol. 31, pp. 271-275.
Marchand et al., "A Novel Approach to the Synthesis of 1,3,3-Trinitroazetidine," J. Org Chem. 1995, vol. 60, No. 15, pp. 4943-4946.
Straessler et al., "Development of a Safe and Efficient Two-Step Synthesis for Preparing 1-Bromoacetyl-3,3-dinitroazetidine, a Novel Clinical Anticancer Candidate," Organic Process Research & Development, 2012, vol. 16, pp. 512-517.

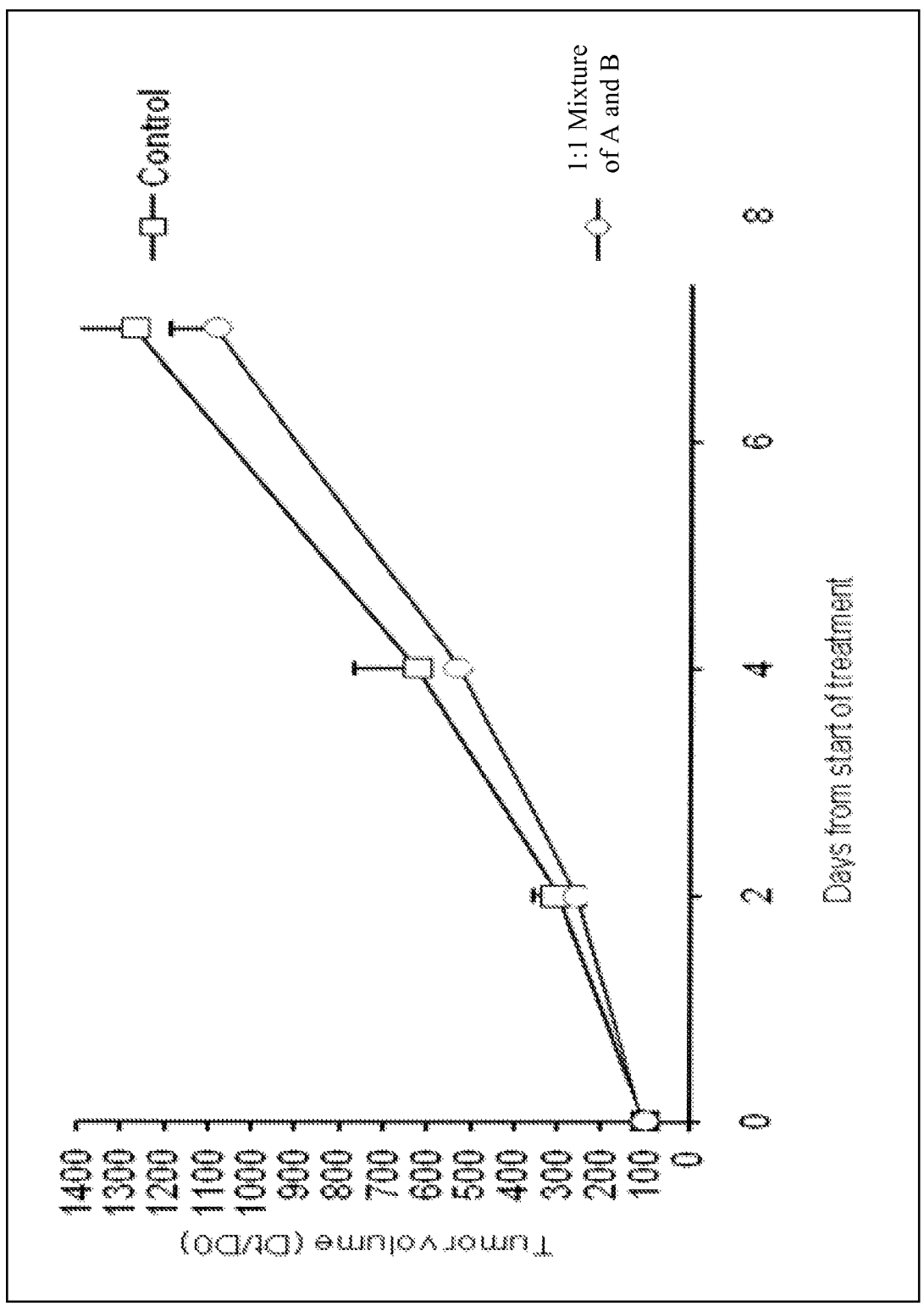

ACYCLIC ORGANONITRO COMPOUNDS FOR USE IN TREATING CANCER

RELATED APPLICATIONS

This application claims the benefit of and priority to U.S. Provisional Patent Application Ser. No. 61/527,745, filed Aug. 26, 2011, the contents of which are hereby incorporated by reference.

FIELD OF THE INVENTION

The invention provides acyclic, geminal-dinitro organic compounds, methods of synthesizing the compounds, pharmaceutical compositions, therapeutic methods, and medical kits. The compounds and pharmaceutical compositions are useful in the treatment of cancer

BACKGROUND

Cancer is a leading cause of death in the United States and many foreign countries. A recent survey by the National Cancer Institute estimates that nearly twelve million Americans have been diagnosed with cancer. Some of the most frequently encountered types of cancer include breast cancer, prostate cancer, skin cancer, colon cancer, rectal cancer, and bladder cancer. Other cancers afflicting a significant number of patients include ovarian cancer, leukemias, brain cancer, lymphomas, uterine cancer, and head and neck cancer.

Current treatment options for cancer typically involve surgery, radiation treatment, and/or chemotherapy. Surgery involves physically removing cancerous tissue. Although surgery is sometimes effective in removing tumors located at certain sites, for example, in the breast, colon, and skin, it cannot be used to treat all types of cancer, such as those located in the backbone or disseminated neoplastic conditions such as leukemia. Radiation therapy involves exposing the patient to ionizing radiation in order to damage the DNA of cancerous cells. Chemotherapy involves administering a chemotherapeutic agent that disrupts cell replication or cell metabolism. Chemotherapy is often used to treat leukemia, breast cancer, lung cancer, and testicular cancer.

Despite the efforts devoted to developing treatments for cancer, current therapeutic options are inadequate because current treatment options frequently have severe side effects and/or are not effective in treating certain types of cancers. For example, the anti-cancer agent 5-fluorouracil has been used to treat various carcinomas, sarcomas, skin cancer, and breast cancer, but this anti-cancer agent causes adverse side effects such as nausea, alopecia, diarrhea, stomatitis, leukocytic thrombocytopenia, and anorexia. The anti-cancer agent cisplatin has been used to treat testicular, ovarian, bladder, head and neck, and esophageal cancer, but this anti-cancer agent has been shown to cause nausea, vomiting, anemia, and reduced white blood cell counts.

Accordingly, the need exists for new therapeutic agents that provide improved efficacy and/or reduced side effects for treating cancer. The present invention addresses this need and provides other related advantages.

SUMMARY

The invention provides acyclic, geminal-dinitro organic compounds, methods of synthesizing the compounds, pharmaceutical compositions, therapeutic methods, and medical kits for treating various conditions using such compounds and pharmaceutical compositions. The compounds and compositions are useful in the treatment of cancer.

Accordingly, one aspect of the invention provides a pharmaceutical composition comprising a pharmaceutically acceptable carrier and at least one compound of Formula I:

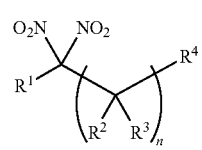

(I)

or a pharmaceutically acceptable salt thereof, wherein the variables are as defined in the detailed description.

Another aspect of the invention provides a compound represented by Formula II:

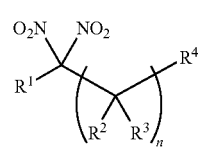

(II)

or a pharmaceutically acceptable salt thereof, wherein the variables are as defined in the detailed description.

The pharmaceutical compositions and compounds can be used to treat medical disorders. Accordingly, another aspect of the invention provides a method of treating cancer in a patient. The method comprises administering to a patient in need thereof a therapeutically effective amount of a pharmaceutical composition described herein or a compound described herein.

BRIEF DESCRIPTION OF FIGURES

FIG. 1 is a graph showing tumor volume in mice after treatment with a mixture of Compound A and Compound B as described in Example 1.

DETAILED DESCRIPTION

The invention provides acyclic, geminal-dinitro organic compounds, methods of synthesizing the compounds, pharmaceutical compositions, therapeutic methods, and medical kits for treating various conditions using such compounds and pharmaceutical compositions. The compounds and compositions are useful in the treatment of cancer. The practice of the present invention employs, unless otherwise indicated, conventional techniques of organic chemistry, pharmacology, and biochemistry. Such techniques are explained in the literature, such as in "Comprehensive Organic Synthesis" (B. M. Trost & I. Fleming, eds., 1991-1992). Various aspects of the invention are set forth below in sections; however, aspects of the invention described in one particular section are not to be limited to any particular section.

Definitions

To facilitate an understanding of the present invention, a number of terms and phrases are defined below.

The terms "a," "an" and "the" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. Unless specified otherwise, alkyl groups can be substituted by one cycloalkyl group. In certain embodiments, the alkyl group is not substituted (i.e., it is unsubstituted).

The term "haloalkyl" refers to an alkyl group that is substituted with at least one halogen, such as fluorine, chlorine, bromine, or iodine. For example, —$CH_2F$, —$CHF_2$, —$CF_3$, —$CH_2CF_3$, —$CF_2CF_3$, and the like.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include cyclohexyl, cyclopentyl, cyclobutyl and cyclopropyl.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" refers to a carbocyclic aromatic group. Representative aryl groups include phenyl, naphthyl, anthracenyl, and the like. Unless specified otherwise, the aromatic ring may be substituted at one or more ring positions with halogen, azide, alkyl, alkenyl, alkynyl, cycloalkyl, hydroxyl, alkoxyl, amino, nitro, carboxylic acid, —C(O)alkyl, —$CO_2$alkyl, carbonyl, carboxyl, carboxamide, or —CN. In certain embodiments, the aryl group is unsubstituted.

The term "heteroaryl" refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. Unless specified otherwise, the heteroaromatic ring may be substituted at one or more ring positions with halogen, azide, alkyl, alkenyl, alkynyl, cycloalkyl, hydroxyl, alkoxyl, amino, nitro, carboxylic acid, —C(O)alkyl, —$CO_2$alkyl, carbonyl, carboxyl, carboxamide, or —CN. In certain embodiments, the heteroaryl group is unsubstituted.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteroatoms include nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include furan, oxirane, 2H-pyran, 4H-pyran, 2H-chromene, and benzofuran. Examples of sulfur-containing heterocyclic rings include thiophene, benzothiophene, and parathiazine. Examples of nitrogen containing rings include pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the heterocyclic group is not substituted (i.e., it is unsubstituted).

The terms "amine" and "amino" refer to both unsubstituted and substituted amines, e.g., a moiety that may be represented by the general formulas:

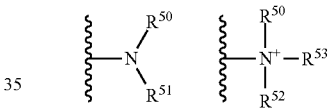

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—$(CH_2)_m$—$R^{61}$, where m and $R^{61}$ are described above.

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, group where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "patient" refers to an organism to be treated by the methods of the present invention. Such organisms may include mammals (e.g., murines, simians, equines, bovines, porcines, canines, felines, and the like), including humans.

As used herein, the term "therapeutically effective amount" refers to the amount of a compound (e.g., a compound of the present invention) or composition comprising a compound of the present invention which is effective for producing some desired therapeutic effect in at least a subpopulation of cells in a patient at a reasonable benefit/risk ratio applicable to any medical treatment. A therapeutically effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent (e.g., a compound of the present invention) with a carrier, inert or active, making the composition especially suitable for diagnostic or therapeutic use in vivo or ex vivo.

As used herein, the term "pharmaceutically acceptable carrier" refers to any of the conventional pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers, and adjuvants, see, e.g., Martin, Remington's Pharmaceutical Sciences, 15th Ed., Mack Publ. Co., Easton, Pa. [1975].

As used herein, the term "pharmaceutically acceptable salt" refers to any salt (e.g., acid or base) of a compound of the present invention which is pharmaceutically acceptable and upon administration to a subject, is capable of providing a compound of this invention or an active metabolite or residue thereof. As is known to those of skill in the art, "salts" of the compounds of the present invention may be derived from inorganic or organic acids and bases. Examples of acids include, for example, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, for example, alkali metal (e.g., sodium) hydroxides, alkaline earth metal (e.g., magnesium), hydroxides, ammonia, and compounds of formula $NW_4^+$, wherein W is $C_{1-4}$ alkyl, and the like.

Examples of salts include, for example, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include, for example, anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage of a compound are by weight unless otherwise specified. Further, if a variable is not accompanied by a definition, then the previous definition of the variable controls.

I. Pharmaceutical Compositions

One aspect of the invention provides pharmaceutical compositions that comprise a pharmaceutically acceptable carrier and at least one compound described herein. For example, in certain embodiments, the invention provides a pharmaceutical composition comprising a pharmaceutically acceptable carrier and at least one compound of Formula I:

(I)

or a pharmaceutically acceptable salt thereof, wherein:

$R^1$ is alkyl, cycloalkyl, —$(C_1$-$C_4)$alkylene-$X^1$, or —$(C_1$-$C_4)$alkylene-$N(R^7)C(O)$-haloalkyl;

$R^2$, $R^3$, and $R^6$ each represent independently for each occurrence hydrogen or alkyl;

$R^4$ is —OH, —OC(O)$R^5$, —N($R^7$)C(O)$R^6$, —C(O)N($R^6$)($R^7$), —N($R^7$)SO$_2R^6$, —SO$_2$N($R^6$)($R^7$), —$X^2$—$(C_1$-$C_6)$alkylene-C(NO$_2$)$_2$-alkyl, or —N($R^6$)C(O)$R^8$; or $R^4$ is —N($R^6$)C(O)-haloalkyl when $R^1$ is —$(C_1$-$C_4)$alkylene-N($R^7$)C(O)-haloalkyl;

$R^5$ represents independently for each occurrence hydrogen, alkyl, cycloalkyl, aryl, heteroaryl, or aralkyl;

$R^7$ represents independently for each occurrence alkyl, —[C($R^2$)$_2$]$_p$-cycloalkyl, —[C($R^2$)$_2$]$_p$-heterocycloalkyl, aryl, or aralkyl;

$R^8$ is —$(C_1$-$C_4)$alkylene-CO$_2$H, —$(C_1$-$C_4)$alkylene-CO$_2$-alkyl, —$(C_1$-$C_4)$alkenylene-CO$_2$H, —$(C_1$-$C_4)$alkenylene-CO$_2$-alkyl, —CF$_3$, or —$(C_1$-$C_4)$alkyl;

$X^1$ is —OH, —OC(O)$R^5$, —N($R^6$)C(O)$R^5$, —C(O)N($R^5$)($R^6$), —N($R^6$)SO$_2R^5$, or —SO$_2$N($R^5$)($R^6$);

$X^2$ is —O—(C$_1$-C$_4$)alkylene-O—, —O—, —OC(O)O—, —N($R^2$)C(O)O—, —OC(O)N($R^2$)—, —N($R^2$)C(O)N($R^2$)—, —N($R^2$)C(S)N($R^2$)—, —N($R^2$)C(O)—, —C(O)N($R^2$)—, —N($R^2$)SO$_2$—, —SO$_2$N($R^2$)—, —OC(O)—, or —CO$_2$—;

n is 1, 2, 3, or 4;

p is 0, 1, 2, 3, or 4; and the stereochemical configuration at any stereocenter in a compound represented by Formula I is R, S, or a mixture thereof.

The invention embraces pharmaceutical compositions containing particular subsets of the family of compounds embraced by Formula I. For example, in certain embodiments, $R^1$ is alkyl or cycloalkyl. In certain embodiments, $R^2$ and $R^3$ are hydrogen. In certain embodiments, $R^4$ is —$X^2$—(C$_1$-C$_6$)alkylene-C(NO$_2$)$_2$-alkyl. In certain embodiments, $X^2$ is —O—(C$_1$-C$_4$)alkylene-O—. In certain other embodiments, $X^2$ is —OC(O)O—. In certain embodiments, n is 1.

One exemplary subset of compounds embraced by Formula I is the following:

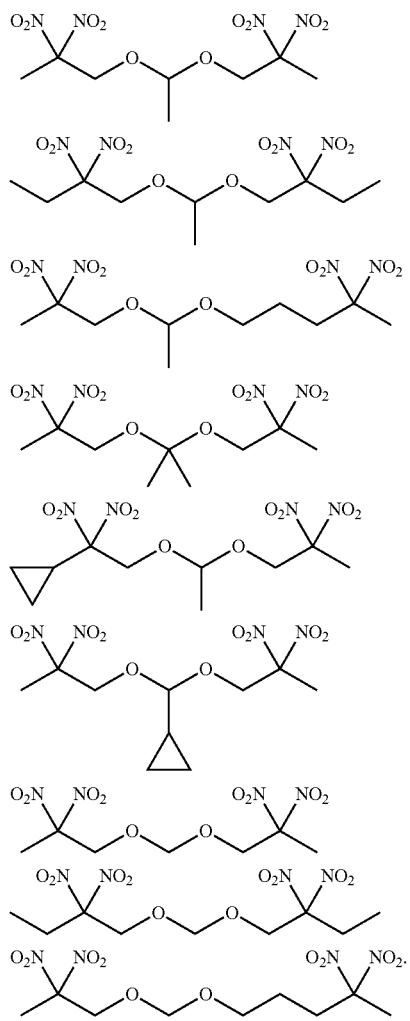

In certain embodiments, the compound is represented by Formula I-A:

or a pharmaceutically acceptable salt thereof, wherein:

$R^1$ is alkyl or cycloalkyl;

$R^2$ and $R^3$ each represent independently for each occurrence hydrogen or alkyl;

$R^4$ is —$X^2$—(C$_1$-C$_6$)alkylene-C(NO$_2$)$_2$-alkyl;

$X^2$ is —O—(C$_1$-C$_4$)alkylene-O—, —O—, —OC(O)O—, —N($R^2$)C(O)O—, —OC(O)N($R^2$)—, —N($R^2$)C(O)N($R^2$)—, —N($R^2$)C(S)N($R^2$)—, —N($R^2$)C(O)—, —C(O)N($R^2$)—, —N($R^2$)SO$_2$—, —SO$_2$N($R^2$)—, —OC(O)—, or —CO$_2$—;

n is 1, 2, 3, or 4; and the stereochemical configuration at any stereocenter in a compound represented by Formula I-A is R, S, or a mixture thereof.

In certain embodiments, the compound is represented by Formula I-A, wherein $X^2$ is —O—(C$_1$-C$_4$)alkylene-O—. In certain other embodiments, $X^2$ is —O—(C$_1$-C$_2$)alkylene-O—. In certain embodiments, $R^1$ is methyl or ethyl. In certain embodiments, $R^2$ and $R^3$ are hydrogen. In certain embodiments, n is 1. In certain embodiments, $R^4$ is —$X^2$—(C$_2$-C$_3$)alkylene-C(NO$_2$)$_2$-methyl. In certain other embodiments, $R^4$ is —$X^2$—(C$_2$-C$_3$)alkylene-C(NO$_2$)$_2$-methyl, $X^2$ is —O—(C$_1$-C$_2$)alkylene-O—, $R^2$ and $R^3$ are hydrogen, and n is 1.

Another subset of compounds embraced by Formula I is where $R^1$ is —(C$_1$-C$_4$)alkylene-N($R^7$)C(O)-haloalkyl, and $R^4$ is —N($R^6$)C(O)-haloalkyl. Further, in certain embodiments, $R^6$ and $R^7$ are alkyl. In certain embodiments, n is 2, and $R^2$ and $R^3$ are hydrogen. Exemplary particular compounds embraced by this subset include, for example, the following:

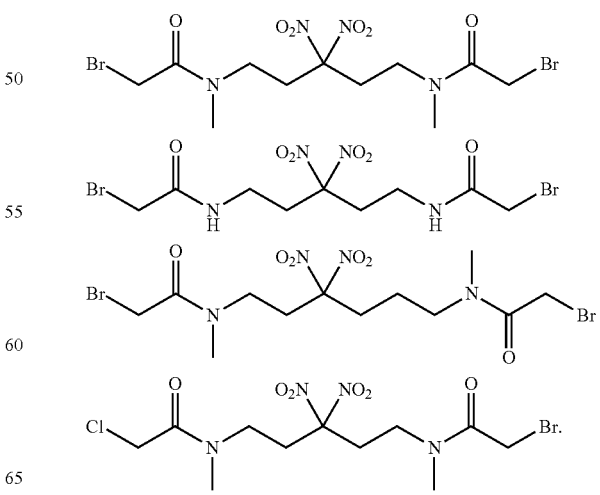

In certain embodiments, the compound is represented by Formula I-B:

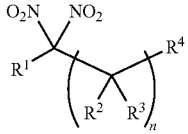
(I-B)

or a pharmaceutically acceptable salt thereof, wherein:
$R^1$ is —$(C_1$-$C_4)$alkylene-N($R^7$)C(O)-haloalkyl;
$R^2$, $R^3$, and $R^6$ each represent independently for each occurrence hydrogen or alkyl;
$R^4$ is —N($R^6$)C(O)-haloalkyl;
$R^7$ is alkyl or —[C($R^2$)$_2$]$_p$-cycloalkyl;
n is 1, 2, 3, or 4;
p is 0, 1, 2, 3, or 4; and
the stereochemical configuration at any stereocenter in a compound represented by Formula I-B is R, S, or a mixture thereof.

In certain embodiments, the compound is represented by Formula I-B, wherein $R^1$ is —$(C_1$-$C_4)$alkylene-N($R^7$)C(O)—$CH_2Br$. In certain embodiments, $R^2$ and $R^3$ are hydrogen. In certain embodiments, $R^4$ is —N($R^6$)C(O)$CH_2Br$. In certain embodiments, $R^7$ is alkyl. In certain embodiments, n is 2. In certain embodiments, $R^1$ is —$(C_1$-$C_4)$alkylene-N(alkyl)C(O)—$CH_2Br$, $R^2$ and $R^3$ are hydrogen, and $R^4$ is —N(alkyl)C(O)$CH_2Br$.

Another subset of compounds embraced by Formula I is where $R^1$ is —$(C_1$-$C_4)$alkylene-$X^1$. In certain embodiments, $X^1$ is —OH or —OC(O)$R^5$. In certain embodiments, $R^4$ is —OH or —OC(O)$R^5$. In certain embodiments, $R^5$ represents independently for each occurrence hydrogen, alkyl or cycloalkyl. In certain embodiments, n is 1, and $R^2$ and $R^3$ are hydrogen. Exemplary particular compounds embraced by this subset include, for example, the following:

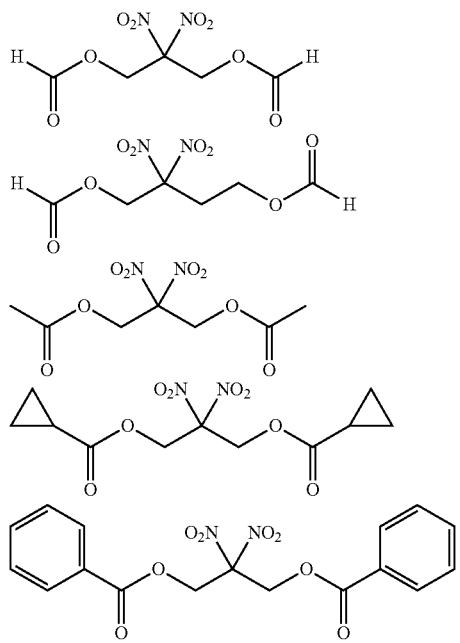

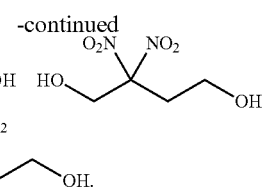

In certain embodiments, the compound is represented by Formula I-C:

(I-C)

or a pharmaceutically acceptable salt thereof, wherein:
$R^1$ is —$(C_1$-$C_4)$alkylene-$X^1$;
$R^2$, $R^3$, and $R^6$ each represent independently for each occurrence hydrogen or alkyl;
$R^4$ is —OH, —OC(O)$R^5$, —N($R^7$)C(O)$R^6$, —C(O)N($R^6$)($R^7$), —N($R^7$)SO$_2R^6$, or —SO$_2$N($R^6$)($R^7$);
$R^5$ represents independently for each occurrence hydrogen, alkyl, cycloalkyl, aryl, heteroaryl, or aralkyl;
$R^7$ is alkyl, —[C($R^2$)$_2$]$_p$-cycloalkyl, —[C($R^2$)$_2$]$_p$-heterocycloalkyl, aryl, or aralkyl;
$X^1$ is —OH, —OC(O)$R^5$, —N($R^6$)C(O)$R^5$, —C(O)N($R^5$)($R^6$), —N($R^6$)SO$_2R^5$, or —SO$_2$N($R^5$)($R^6$);
n is 1, 2, 3, or 4;
p is 0, 1, 2, 3, or 4; and
the stereochemical configuration at any stereocenter in a compound represented by Formula I-C is R, S, or a mixture thereof.

In certain embodiments, the compound is represented by Formula I-C, wherein $R^1$ is —$CH_2$—$X^1$. In certain embodiments, $R^2$ and $R^3$ are hydrogen. In certain embodiments, $R^4$ is —OC(O)$R^5$. In certain other embodiments, $R^4$ is —N($R^7$)C(O)$R^6$ or —C(O)N($R^6$)($R^7$). In certain embodiments, $R^5$ is hydrogen, alkyl, or cycloalkyl. In certain embodiments, $R^7$ represents independently for each occurrence alkyl or —[C($R^2$)$_2$]$_p$-cycloalkyl. In certain embodiments, $X^1$ is —OC(O)$R^5$. In certain other embodiments, $X^1$ is —N($R^6$)C(O)$R^5$ or —C(O)N($R^5$)($R^6$). In certain other embodiments, $R^1$ is —$CH_2$—$X^1$, $R^2$ and $R^3$ are hydrogen, $R^4$ is —OC(O)$R^5$, and $X^1$ is —OC(O)$R^5$.

In certain embodiments, the compound is one of the compounds in Tables 1-3.

TABLE 1

| No. | X | Y | Z |
|---|---|---|---|
| I-1 | —$CH_3$ | —OCH$_2$O— | —$CH_3$ |
| I-2 | —$CH_3$ | —OCH$_2$O— | —$CH_2CH_3$ |
| I-3 | —$CH_3$ | —OCH(CH$_3$)O— | —$CH_3$ |
| I-4 | —$CH_3$ | —OCH(CH$_3$)O— | —$CH_2CH_3$ |
| I-5 | —$CH_3$ | —OCH(CH$_3$)OCH$_2$— | —$CH_3$ |
| I-6 | —$CH_3$ | —OCH(CH$_3$)OCH$_2$— | —$CH_2CH_3$ |
| I-7 | —$CH_3$ | —OC(CH$_3$)$_2$OCH$_2$— | —$CH_3$ |
| I-8 | —$CH_3$ | —OC(CH$_3$)$_2$OCH$_2$— | —$CH_2CH_3$ |

TABLE 1-continued $$O_2N\underset{X}{\overset{NO_2}{\diagdown}}\overset{}{\diagup}Y\overset{}{\diagdown}\underset{Z}{\overset{O_2N\ NO_2}{\diagup}}$$

| No. | X | Y | Z |
|---|---|---|---|
| I-9 | —CH$_3$ | O | —CH$_3$ |
| I-10 | —CH$_2$CH$_3$ | O | —CH$_2$CH$_3$ |
| I-11 | —CH$_3$ | —OC(O)O— | —CH$_3$ |
| I-12 | —CH$_2$CH$_3$ | —OC(O)O— | —CH$_2$CH$_3$ |
| I-13 | —CH$_3$ | —N(H)C(O)O— | —CH$_3$ |
| I-14 | cyclopropyl | —N(H)C(O)O— | —CH$_2$CH$_3$ |
| I-15 | —CH$_3$ | —OC(O)N(H)— | —CH$_3$ |
| I-16 | cyclobutyl | —OC(O)N(H)— | —CH$_3$ |
| I-17 | —CH$_3$ | —N(H)C(O)N(H)— | —CH$_3$ |
| I-18 | —CH$_2$CH$_3$ | —N(H)C(O)N(H)— | —CH$_2$CH$_3$ |
| I-19 | —CH$_3$ | —N(H)C(O)— | —CH$_3$ |
| I-20 | —CH$_2$CH$_3$ | —N(H)C(O)— | —CH$_2$CH$_3$ |
| I-21 | —CH$_3$ | —N(H)C(O)— | —CH$_2$CH$_3$ |
| I-22 | —CH$_2$CH$_3$ | —N(H)C(O)— | —CH$_2$CH$_3$ |
| I-23 | —CH$_3$ | —N(H)SO$_2$— | —CH$_3$ |
| I-24 | cyclopropyl | —N(H)SO$_2$— | cyclobutyl |
| I-25 | —CH$_3$ | —SO$_2$N(H)— | —CH$_3$ |
| I-26 | cyclobutyl | —SO$_2$N(H)— | —CH$_3$ |
| I-27 | —CH$_3$ | —OC(O)— | —CH$_3$ |
| I-28 | —CH$_3$ | —OC(O)— | —CH$_2$CH$_3$ |
| I-29 | —CH$_3$ | —CO$_2$— | —CH$_3$ |
| I-30 | —CH$_3$ | —CO$_2$— | —CH$_2$CH$_3$ |

TABLE 2

$$X\overset{}{\diagdown}\underset{}{\overset{O_2N\ NO_2}{\diagup}}\overset{}{\diagdown}Y$$

| No. | X | Y |
|---|---|---|
| II-1 | —OH | —OH |
| II-2 | —CH$_2$OH | —CH$_2$OH |
| II-3 | —OC(O)H | —OC(O)H |
| II-4 | —CH$_2$OC(O)H | —CH$_2$OC(O)H |
| II-5 | —OC(O)CH$_3$ | —OC(O)CH$_3$ |
| II-6 | —OC(O)CH$_2$CH$_3$ | —OC(O)CH$_2$CH$_3$ |
| II-7 | —OC(O)CH(CH$_3$)$_2$ | —OC(O)CH(CH$_3$)$_2$ |
| II-8 | —OC(O)-cyclopropyl | —OC(O)-cyclopropyl |
| II-9 | —OC(O)-phenyl | —OC(O)-phenyl |
| II-10 | —OC(O)-(4-pyridyl) | —OC(O)-(4-pyridyl) |
| II-11 | —OC(O)-(2-furyl) | —OC(O)-(2-furyl) |
| II-12 | —N(H)C(O)CH$_3$ | —N(H)C(O)CH$_3$ |
| II-13 | —N(H)C(O)-cyclopropyl | —N(H)C(O)-cyclopropyl |
| II-14 | —N(H)C(O)-phenyl | —N(H)C(O)-phenyl |
| II-15 | —N(CH$_3$)C(O)CH$_2$Br | —N(CH$_3$)C(O)CH$_2$Br |
| II-16 | —CH$_2$N(CH$_3$)C(O)CH$_2$Br | —CH$_2$N(CH$_3$)C(O)CH$_2$Br |
| II-17 | —CH$_2$N(CH$_3$)C(O)CH$_2$Cl | —CH$_2$N(CH$_3$)C(O)CH$_2$Cl |
| II-18 | —CH$_2$CH$_2$N(CH$_3$)C(O)CH$_2$Br | —CH$_2$CH$_2$N(CH$_3$)C(O)CH$_2$Br |
| II-19 | —N(H)SO$_2$CH$_3$ | —N(H)SO$_2$CH$_3$ |
| II-20 | —N(H)SO$_2$CH$_3$ | —N(H)SO$_2$CH$_3$ |
| II-21 | —OH | —OC(O)CH$_3$ |
| II-22 | —OH | —OC(O)-phenyl |
| II-23 | —OC(O)-(2-furyl) | —OC(O)H |
| II-24 | —N(H)C(O)CH$_3$ | —N(CH$_3$)C(O)CH$_2$Br |
| II-25 | —N(H)SO$_2$CH$_3$ | —CH$_2$N(CH$_3$)C(O)CH$_2$Cl |

TABLE 3

$$X\overset{}{\diagdown}\underset{}{\overset{O_2N\ NO_2}{\diagup}}(\ )_p\overset{Y}{\underset{\underset{O}{\|}}{N}}Z$$

| No. | X | P | Y | Z |
|---|---|---|---|---|
| III-1 | —H | 1 | —CH$_3$ | —CH$_2$CH$_2$CO$_2$H |
| III-2 | —H | 1 | H | —CH$_2$CH$_2$CO$_2$H |
| III-3 | —H | 1 | —CH$_3$ | —CH=CHCO$_2$H |
| III-4 | —H | 1 | H | —CH=CHCO$_2$H |
| III-5 | —H | 1 | —CH$_3$ | —CF$_3$ |
| III-6 | —H | 1 | H | —CF$_3$ |
| III-7 | —H | 1 | —CH$_3$ | —CH$_3$ |
| III-8 | —H | 1 | H | —CH$_3$ |
| III-9 | —H | 2 | —CH$_3$ | —CH$_2$CH$_2$CO$_2$H |
| III-10 | —H | 2 | H | —CH$_2$CH$_2$CO$_2$H |
| III-11 | —H | 2 | —CH$_3$ | —CH=CHCO$_2$H |
| III-12 | —H | 2 | H | —CH=CHCO$_2$H |
| III-13 | —H | 2 | —CH$_3$ | —CF$_3$ |
| III-14 | —H | 2 | H | —CF$_3$ |
| III-15 | —H | 2 | —CH$_3$ | —CH$_3$ |
| III-16 | —H | 2 | H | —CH$_3$ |
| III-17 | —CH$_3$ | 1 | —CH$_3$ | —CH$_2$CH$_2$CO$_2$H |
| III-18 | —CH$_3$ | 1 | —CH$_3$ | —CH=CHCO$_2$H |
| III-19 | —CH$_3$ | 1 | —CH$_3$ | —CF$_3$ |
| III-20 | —CH$_3$ | 1 | H | —CH$_3$ |
| III-21 | cyclopropyl | 1 | —CH$_3$ | —CH$_2$CH$_2$CO$_2$H |
| III-22 | cyclopropyl | 1 | —CH$_3$ | —CH=CHCO$_2$H |
| III-23 | cyclopropyl | 1 | —CH$_3$ | —CF$_3$ |
| III-24 | cyclopropyl | 1 | H | —CH$_3$ |

Methods for preparing compounds described herein are illustrated in the following synthetic schemes. The following schemes are given for the purpose of illustrating the invention, but not for limiting the scope or spirit of the invention.

Scheme 1 provides an exemplary procedure for preparing compounds having two geminal-dinitro groups connected by a heteroatom-containing linker, such as the compounds shown in Table 1 above. The reaction entails the condensation of two geminal-dinitro alcohols A and B with an electrophile C (depicted as an aldehyde in Scheme 1) to produce the corresponding heteroatom-linked geminal-dinitro dimer D (depicted with oxygen atoms in Scheme 1). Each of m and n in geminal-dinitro alcohol A and x and y in geminal-dinitro alcohol B may be a positive integer greater than or equal to one, and each of n, m, x, and y may or may not be the same. Consequently, heteroatom-linked geminal-dinitro dimer D may or may not be symmetrical. U.S. Pat. Nos. 5,449,835 and 5,648,556 describe the preparation of Compounds I-1 and I-3, respectively, of Table 1. To form Compounds I-1 and I-3, 2,2-dinitropropanol is condensed with an aldehyde (formaldehyde or acetaldehyde) in the presence of an acid catalyst to give Compound I-1 or Compound I-3. Similar procedures may be used to prepare Compounds I-2 and I-4 through I-8 in Table 1 by changing the electrophile C. For example, acetone may be used as the electrophile C to produce Compounds I-7 and I-8. Derivatives of D having various heteroatom linkers may be synthesized by varying the electrophile C.

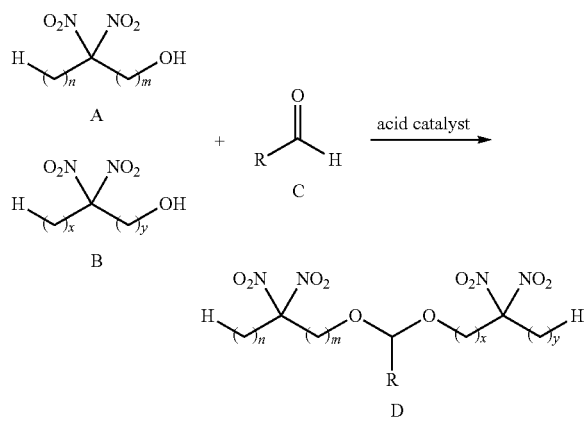

Scheme 1.

R is hydrogen, alkyl, cycloalkyl, aryl and the like;
n, m, x, and y are independently 1, 2, 3, etc.

Scheme 2 provides an exemplary procedure for preparing α,ω-difunctional-geminal-dinitro alkyl compounds, such as compounds in Table 2 above. Esterification of alkyl-diol A using the desired acid anhydride B in the presence of base provides the diester (or diformate when R is hydrogen) C. Further description of exemplary procedures for esterification reactions involving diol starting materials is provided in, for example, U.S. Pat. No. 6,425,966, which is hereby incorporated by reference.

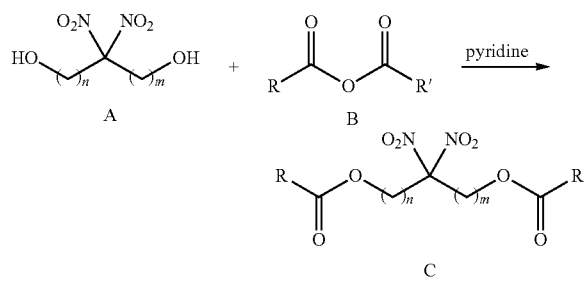

R is hydrogen, alkyl, cycloalkyl, aryl and the like;
R' is alkyl, cycloalkyl, aryl and the like;
n and m are independently 1, 2, 3, or 4.

Scheme 3 provides an exemplary procedure for preparing geminal-dinitro alkyl amide compounds, such as compounds in Table 3 above. Reaction of dialkyl amine A and hydroxy-dinitroalkane B provides dinitroalkylamine C. Reaction of dinitroalkylamine C with a Lewis Acid and an acylating agent (e.g., an acid halide, such as XC(O)R' where X is, for example, Cl or Br) provides dinitroalkylamide D. The starting dialkyl amine A and hydroxy-dinitroalkane B can be obtained from commercial sources or prepared based on procedures described in the literature. For a description of procedures to make dinitro-organic compounds, see, for example, Kornblum et al. in *J. Org. Chem.* (1983) vol. 48, 332-337; Hiskey et al. in *Journal of Energetic Materials* (1999) vol. 17, 233-254; and Agrawal et al. in *Organic Chemistry of Explosives,* Wiley & Sons, England, 2007. Further, if a particular compound contains a functional group sensitive to one or more of the synthetic transformations described herein, then conventional protecting group strategies are contemplated to be applied. For a description of protecting group strategies and procedures, see, for example, Greene, T. W.; Wuts, P. G. M. *Protective Groups in Organic Synthesis,* $2^{nd}$ ed.; Wiley, New York, 1991.

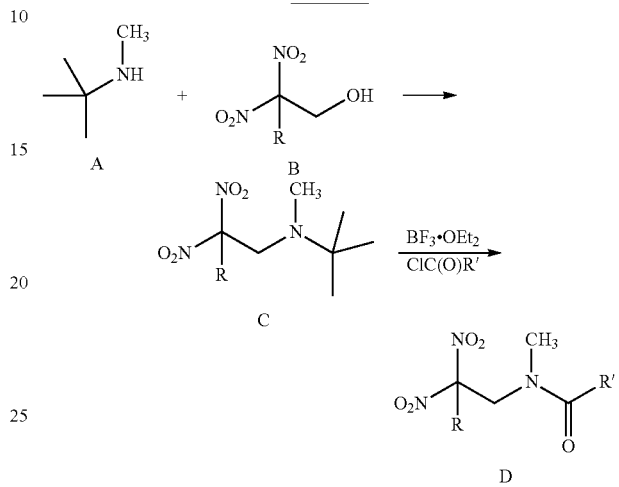

R is alkyl or cycloalkyl;
R' is optionally substituted alkyl, alkenyl, cycloalkyl, aryl and the like.

Scheme 4 provides an alternative exemplary procedure for preparing geminal-dinitro alkyl amide compounds. Reaction of hydroxy-dinitroalkane A with trifluoromethanesulfonic anhydride (($CF_3SO_2)_2O$; abbreviated $Tf_2O$) provides dinitroalkyltriflate B, which upon reaction with trimethylsilylazide ($TMSN_3$) provides dinitroalkylazide C. The azide group of C can be selectively reduced to the amine and reacted with an acylating agent (e.g., XC(O)R' in the presence of base, where X is, for example, Cl or Br) to provide dinitroalkylamide D.

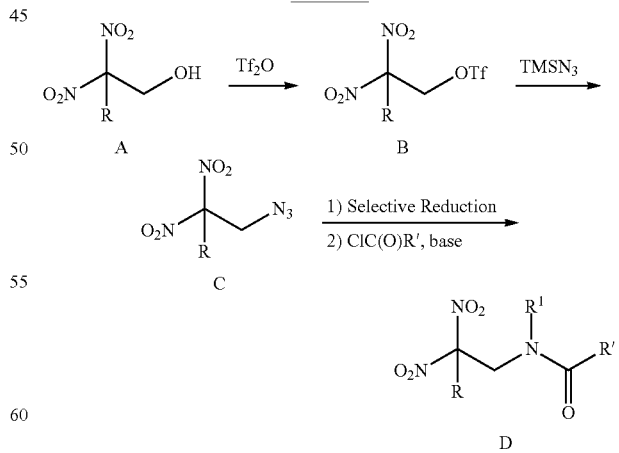

R is alkyl or cycloalkyl;
R' is optionally substituted alkyl, alkenyl, cycloalkyl, aryl and the like.

Scheme 5 provides another alternative exemplary procedure for preparing geminal-dinitro alkyl amide compounds.

Reaction of hydroxy-dinitroalkane A with aryl sulfonamide B under Fukuyama-Mitsunobu conditions (using, for example, tributylphosphine (Bu₃P) and diisopropyl azodicarboxylate (DIAD)) provides dinitroalkylsulfonamide C. For additional information, see, for example, Fukuyama et al. in *Tetrahedron Letters* (1995) 36, 6373. Reaction of sulfonamide C with 2-mercaptoethanol followed by addition of an acylating agent (e.g., XC(O)R″ in the presence of base, where X is, for example, Cl or Br) provides dinitroalkylamide D.

Scheme 5.

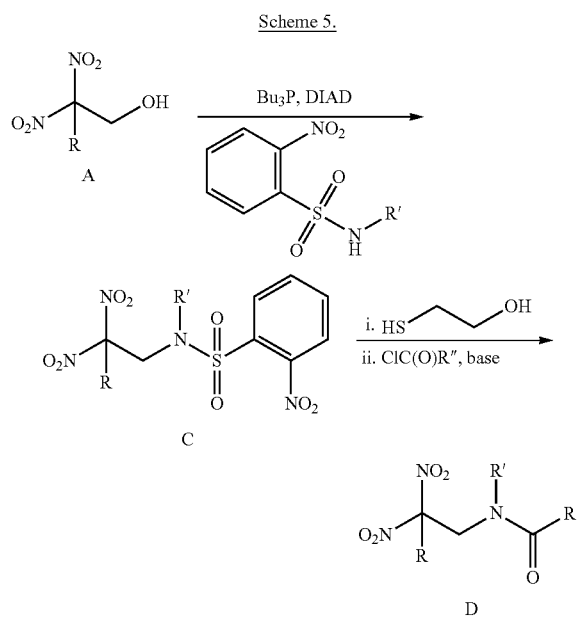

R is alkyl or cycloalkyl;
R′ is alkyl; and
R″ is optionally substituted alkyl, alkenyl, cycloalkyl, aryl and the like.

Scheme 6 provides another alternative exemplary procedure for preparing geminal-dinitro alkyl amide compounds. Reaction of nitroalkane A with aldehyde B provides α-hydroxy-nitroalkane C, which upon dehydration provides nitroalkene D. Reaction of nitroalkene D with an amine provides α-amino-nitroalkane E that can be converted to dinitroalkane F, which is acylated to provide dinitroalkylamide G. For additional description of synthetic procedures for converting a mono-nitro alkane to a geminal dinitro-alkane, see, for example, Kornblum et al. in *J. Org. Chem.* (1983) vol. 48, 332-337.

Scheme 6.

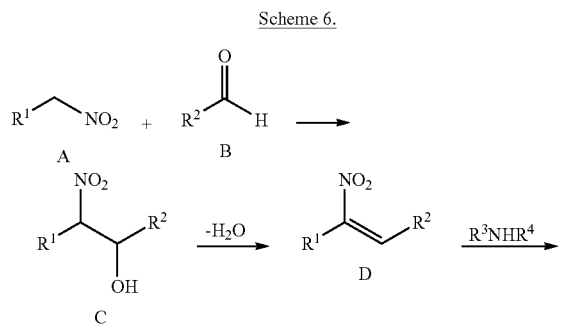

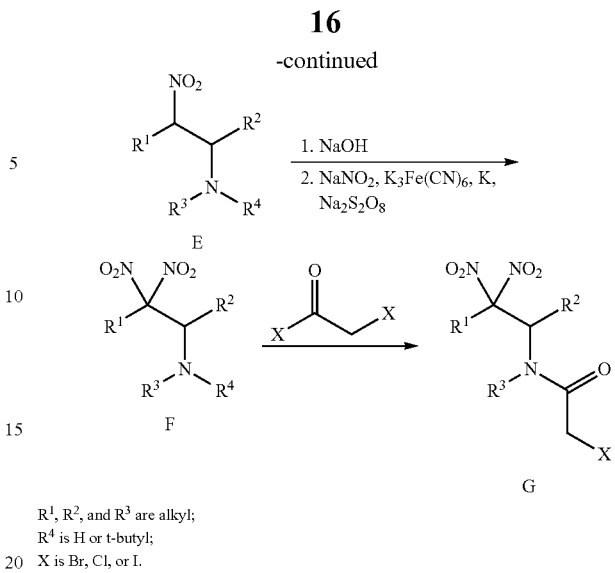

$R^1$, $R^2$, and $R^3$ are alkyl;
$R^4$ is H or t-butyl;
X is Br, Cl, or I.

II. Exemplary Acyclic Geminal Dinitro Compounds

Another aspect of the invention provides a compound represented by Formula II:

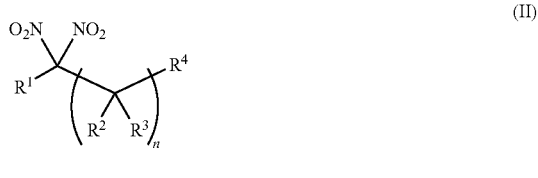

(II)

or a pharmaceutically acceptable salt thereof, wherein:

$R^1$ is $(C_2-C_6)$alkyl, cycloalkyl, or —$(C_1-C_4)$alkylene-N$(R^5)$C(O)-haloalkyl;

$R^2$, $R^3$, and $R^6$ each represent independently for each occurrence hydrogen or alkyl;

$R^4$ is —X—$(C_1-C_6)$alkylene-C(NO$_2$)$_2$-alkyl; or $R^4$ is —N$(R^6)$C(O)-haloalkyl when $R^1$ is —$(C_1-C_4)$alkylene-N$(R^5)$C(O)-haloalkyl;

$R^5$ represents independently for each occurrence alkyl, —[C(R$^2$)$_2$]$_p$-cycloalkyl, —[C(R$^2$)$_2$]$_p$-heterocycloalkyl, aryl, or aralkyl;

X is —O—$(C_1-C_4)$alkylene-O—, —O—, —OC(O)O—, —N(R$^2$)C(O)O—, —OC(O)N(R$^2$)—, —N(R$^2$)C(O)N(R$^2$)—, —N(R$^2$)C(S)N(R$^2$)—, —N(R$^2$)C(O)—, —C(O)N(R$^2$)—, —N(R$^2$)SO$_2$—, —SO$_2$N(R$^2$)—, —OC(O)—, or —CO$_2$—;

n is 1, 2, 3, or 4;

p is 0, 1, 2, 3, or 4; and the stereochemical configuration at any stereocenter in a compound represented by Formula II is R, S, or a mixture thereof.

In certain embodiments, the compound of Formula II contains two sets of geminal dinitro groups separated by an oxygenated linker, such as where $R^1$ is $(C_2-C_6)$alkyl or cycloalkyl, and $R^4$ is —X—$(C_1-C_6)$alkylene-C(NO$_2$)$_2$-alkyl. In certain embodiments, X is —O—$(C_1-C_4)$alkylene-O—. In certain embodiments, $R^2$ and $R^3$ are hydrogen, and n is 1. In certain other embodiments, $R^1$ is $(C_3-C_6)$alkyl. In certain other embodiments, $R^1$ is cycloalkyl. Accordingly, in certain embodiments, the compound can be, for example, one of the following:

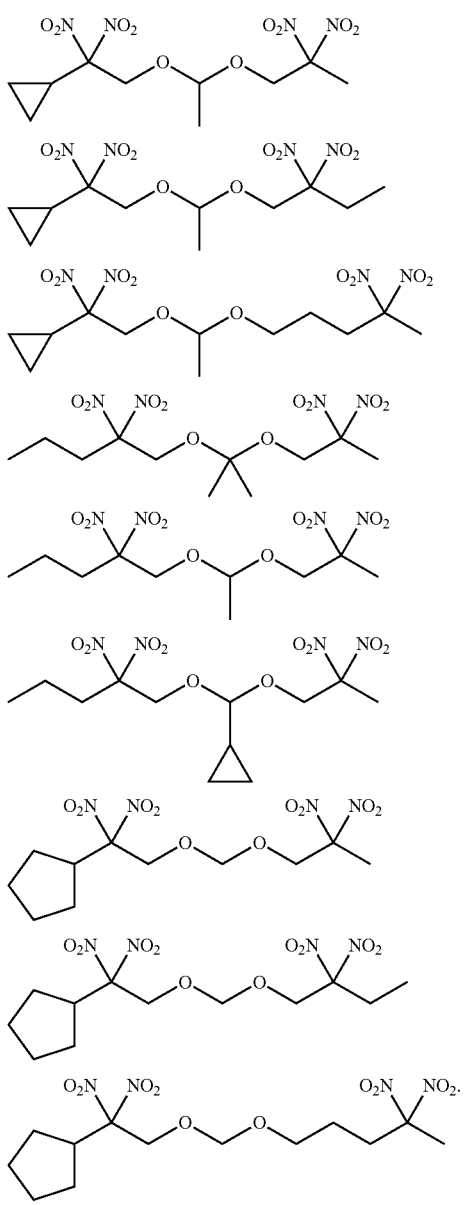

In certain other embodiments, the compound of Formula II has one geminal dinitro group and two alpha-haloamide groups, such as where $R^1$ is —$(C_1-C_4)$alkylene-$N(R^5)C(O)$-haloalkyl, and $R^4$ is —$N(R^6)C(O)$-haloalkyl. In certain embodiments, $R^5$ and $R^6$ are alkyl. In certain embodiments, n is 2, and $R^2$ and $R^3$ are hydrogen. For example, the compound may be one of the following:

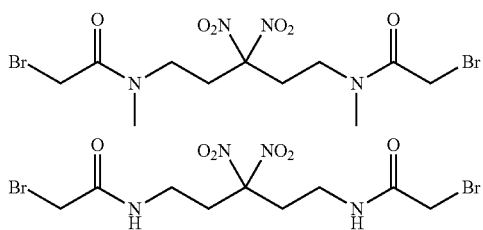

-continued

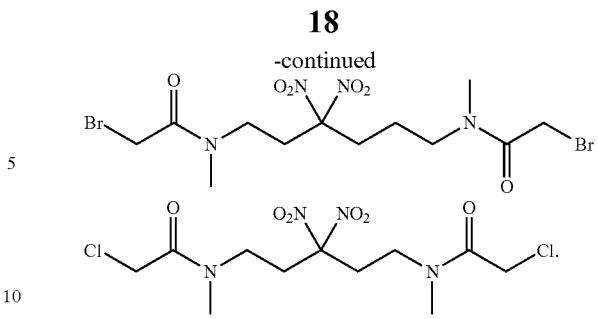

Compounds described in Section II can be prepared based on the procedures described in Section I above.

III. Therapeutic Applications

The pharmaceutical compositions and compounds described herein can be used to treat cancer. Accordingly, one aspect of the invention provides a method of treating cancer in a patient. The method comprises administering to a patient in need thereof a therapeutically effective amount of a pharmaceutical composition described herein or a compound described herein (such as a compound of Formula I or II) in order to treat the cancer. In certain embodiments, a combination of two or more of the compounds described herein (such as a combination of the compounds of Formula I or II) may be administered to the patient to treat the cancer.

In certain embodiments, the cancer is a solid tumor. In certain other embodiments, the cancer is squamous cell carcinoma, basal cell carcinoma, breast cancer, prostate cancer, skin cancer, small cell lung cancer, non-small cell lung cancer, colon cancer, pancreatic cancer, rectal cancer, bladder cancer, ovarian cancer, brain cancer, uterine cancer, cervical cancer, testicular cancer, head and neck cancer, a leukemia, or a lymphoma (e.g., Non-Hodgkin Lymphoma). In certain other embodiments, the cancer is a sweat gland carcinoma, sebaceous gland carcinoma, endometrial cancer, stomach cancer, thyroid cancer, kidney cancer, uterus cancer, espophagus cancer, or liver cancer. In certain other embodiments, the cancer is breast cancer, prostate cancer, skin cancer, small cell lung cancer, non-small cell lung cancer, colon cancer, pancreatic cancer, rectal cancer, bladder cancer, or ovarian cancer. In certain other embodiments, the cancer is breast cancer, prostate cancer, skin cancer, or colon cancer. In certain other embodiments, the cancer is squamous cell carcinoma.

In certain embodiments, the patient is a human.

IV. Medical Kits

Another aspect of the invention provides a medical kit. The medical kit contains (i) a pharmaceutical composition described herein or a compound described herein (such as a compound of Formula I or II), and (ii) instructions for treating a medical disorder, such as cancer.

V. Pharmaceutical Carriers, Form of Pharmaceutical Compositions, and Dosing Considerations The pharmaceutical compositions comprise one or more of the compounds described above (as the active ingredient), formulated together with one or more pharmaceutically acceptable carriers. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, from about 5 percent to about 70 percent of active ingredient, or from about 10 percent to about 30 percent of active ingredient.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

In certain embodiments, the pharmaceutical compositions or compounds may be administered to the patient by systemic administration. The term "systemic administration" as used herein means the administration of a compound, drug or other material other than directly into the central nervous system, such that it enters the patient's system and, thus, is subject to metabolism and other like processes, for example, subcutaneous administration.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, the daily dose of a compound of the invention is that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated treatment of cancer, will range from about 0.0001 to about 100 mg per kilogram of body weight per day. In certain other embodiments, the daily dose of a compound of the invention corresponds to the maximum tolerated dose.

If desired, the effective daily dose of the active compound may be administered as two, three, four, five, six or more sub-doses administered separately at appropriate intervals throughout the day, optionally, in unit dosage forms. Preferred dosing is one administration per day.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the patient being treated. Single or multiple administrations are carried out with the dose level and pattern being selected by the treating physician.

Suitable dosage formulations and methods of administering the compounds are readily determined by those of skill in the art. Preferably, the compounds are administered at about 0.01 mg/kg to about 200 mg/kg, at about 0.1 mg/kg to about 100 mg/kg, or at about 0.5 mg/kg to about 50 mg/kg. When the compounds described herein are co-administered with another agent (e.g., a sensitizing agent), the effective amount of the compound may be less than when the compound is used alone.

The description above describes multiple aspects and embodiments of the invention, including compounds, pharmaceutical compositions, therapeutic methods, and medical kits. The patent application specifically contemplates all combinations and permutations of the aspects and embodiments. For example, the invention contemplates treating breast cancer in a human patient by administering a therapeutically effective amount a pharmaceutical composition comprising compound of Formula I, particularly a compound of Formula I-A. Further, for example, the invention contemplates all combinations and permutations of the aspects and embodiments of the synthetic methods described herein, such as the methods of synthesizing the compounds of Formula I and II.

EXAMPLES

The invention now being generally described, will be more readily understood by reference to the following examples, which are included merely for purposes of illustration of certain aspects and embodiments of the present invention, and are not intended to limit the invention.

Example 1

Anti-Cancer Assay

Mice with SCC VII tumors were treated with a 1:1 mixture of Compound A and Compound B. Experimental procedures are results are provided below.
Part I—Experimental Procedures
Treatment Composition:

The Treatment Composition was a 1:1 mixture of Compound A and Compound B in a water/DMSO carrier. The mixture of Compound A and Compound B was present at a concentration of 0.6 mg/mL. The concentration of dimethylsulfoxide (DMSO) in the Treatment Composition was 0.6%.

Compound A has the formula:

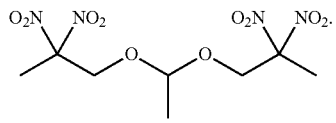 [SMILES: CC(OCC(C)([N+](=O)[O-])[N+](=O)[O-])OCC(C)([N+](=O)[O-])[N+](=O)[O-]]

Compound A can be prepared according to the procedures described in U.S. Pat. No. 5,648,556, which is hereby incorporated by reference. Compound B has the formula:

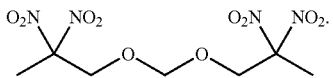 [SMILES: CC(COCOCC(C)([N+](=O)[O-])[N+](=O)[O-])([N+](=O)[O-])[N+](=O)[O-]]

Compound B can be prepared according to the procedures described in U.S. Pat. No. 5,449,835, which is hereby incorporated by reference.

Study Procedures:

Male C3H mice were obtained from Charles River Laboratories and maintained under specific pathogen-free conditions. Mice were housed five animals per cage and autoclaved food and water was provided ad libitum. Cages were located in rooms having a temperature of 65±2 degrees Fahrenheit, a humidity of 50%±5%, and a 12-hour day-and-night light cycle. Mice were 7-8 weeks old, with a body weight in the range of 22-25 grams, at the time inoculated with tumor cells.

Mice were inoculated subcutaneously with $5\times10^5$ SCCVII tumor cells in 0.05 mL Hank's solution on the back. Ten days after tumor implantation, treatment was initiated (Day 0) by administering the Treatment Composition by intraperitoneal injection every other day (i.e., q.o.d on Days 0, 2, and 4) for 3 doses total. The length and width of the tumors were measured with calipers immediately before treatment and three times a week thereafter until the tumor volume reached at least four times (4×) the original pre-treatment volume. Tumor volume (mm³) was calculated according to the formula:

Tumor Volume=π/6×length×width

Part II—Results

Tumors in mice that received the Treatment Composition were smaller than tumors in mice that did not receive treatment. Experimental data showing tumor volume in treated and untreated (control) mice are provided in FIG. 1.

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A pharmaceutical composition comprising a pharmaceutically acceptable carrier and at least one compound of Formula I:

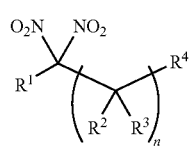

(I)

or a pharmaceutically acceptable salt thereof, wherein:
$R^1$ is alkyl, cycloalkyl, or —(C$_1$-C$_4$)alkylene-N(R$^7$)C(O)-haloalkyl;
$R^2$, $R^3$, and $R^6$ each represent independently for each occurrence hydrogen or alkyl;
$R^4$ is —X$^2$—(C$_1$-C$_6$)alkylene-C(NO$_2$)$_2$-alkyl; or $R^4$ is —N(R$^6$)C(O)-haloalkyl when $R^1$ is —(C$_1$-C$_4$)alkylene-N(R$^7$)C(O)-haloalkyl;
$R^7$ is alkyl;
$X^2$ is —O—(C$_1$-C$_4$)alkylene-O—;
n is 1, 2, or 3; and
the stereochemical configuration at any stereocenter in a compound represented by Formula I is R, S, or a mixture thereof.

2. The pharmaceutical composition of claim 1, wherein $R^1$ is alkyl or cycloalkyl.

3. The pharmaceutical composition of claim 1, wherein $R^2$ and $R^3$ are hydrogen.

4. The pharmaceutical composition of claim 2, wherein $R^4$ is —X$^2$—(C$_1$-C$_6$)alkylene-C(NO$_2$)$_2$-alkyl.

5. The pharmaceutical composition of claim 1, wherein n is 1.

6. The pharmaceutical composition of claim 1, wherein the at least one compound is one of the following:

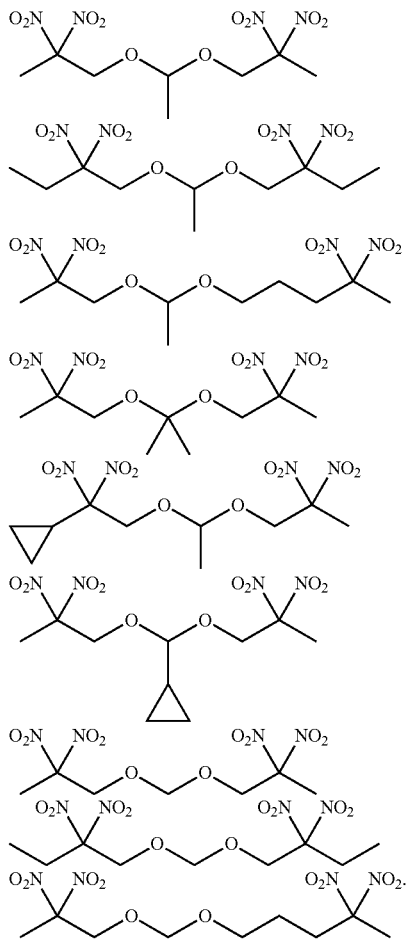

7. The pharmaceutical composition of claim 1, wherein $R^1$ is —(C$_1$-C$_4$)alkylene-N(R)C(O)-haloalkyl, and $R^4$ is —N(R$^6$)C(O)-haloalkyl.

8. The pharmaceutical composition of claim 7, wherein $R^6$ and $R^7$ are alkyl.

9. The pharmaceutical composition of claim 8, wherein n is 2, and $R^2$ and $R^3$ are hydrogen.

10. A pharmaceutical composition comprising a pharmaceutically acceptable carrier and at least one compound selected from the following:

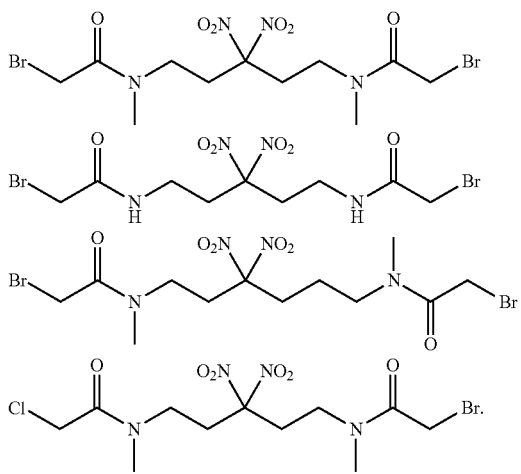

11. A method of treating cancer in a patient, comprising administering to a patient in need thereof a therapeutically effective amount of a pharmaceutical composition of claim 1 in order to treat the cancer, wherein the cancer is squamous cell carcinoma, prostate cancer, skin cancer, small cell lung cancer, non-small cell lung cancer, bladder cancer, or cervical cancer.

12. A pharmaceutical composition comprising a pharmaceutically acceptable carrier and at least one compound of Formula I-C:

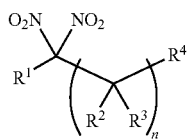

(I-C)

or a pharmaceutically acceptable salt thereof, wherein:
$R^1$ is —$(C_1$-$C_4)$alkylene-OH or —$(C_1$-$C_4)$alkylene-OC(O)$R^5$;

$R^2$, $R^3$, and $R^6$ each represent independently for each occurrence hydrogen or alkyl;

$R^4$ is —OH or —OC(O)$R^5$;

$R^5$ represents independently for each occurrence hydrogen, alkyl, cycloalkyl, or aryl;

n is 1, 2, or 3; and the stereochemical configuration at any stereocenter in a compound represented by Formula I-C is R, S, or a mixture thereof.

13. The pharmaceutical composition of claim 12, wherein the compound is one of the following:

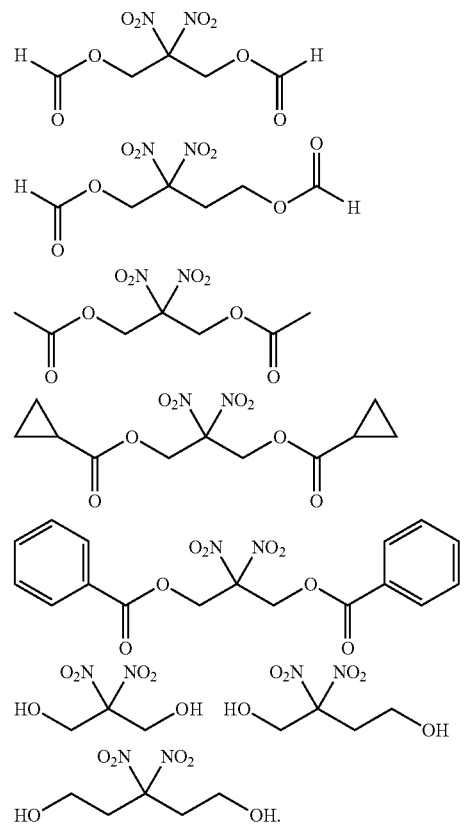

* * * * *